(12) United States Patent
Belfield et al.

(10) Patent No.: US 7,253,287 B1
(45) Date of Patent: Aug. 7, 2007

(54) REACTIVE PROBES FOR TWO-PHOTON FLUORESCENT IMAGING AND SENSING

(75) Inventors: Kevin D. Belfield, Oviedo, FL (US); Katherine J. Schafer, Orlando, FL (US)

(73) Assignee: Research Foundation of The University of Central Florida, Inc., Orlando, FL (US)

( * ) Notice: Subject to any disclaimer, the term of this patent is extended or adjusted under 35 U.S.C. 154(b) by 130 days.

(21) Appl. No.: 11/128,497

(22) Filed: May 13, 2005

Related U.S. Application Data (60) Provisional application No. 60/571,202, filed on May 14, 2004.

(51) Int. Cl.
*C07D 277/66* (2006.01)
(52) U.S. Cl. ..................................... 548/160
(58) Field of Classification Search ................ 548/160
See application file for complete search history.

(56) References Cited

OTHER PUBLICATIONS

Belfield, et al., "Reactive two-photon fluorescent probes for biological imaging", Aug. (2003), pp. 91-95, Proceedings of SPIE, vol. 5211.*

Katherine Schafer, et al., "Fluorescent dyes for multiphoton bio-imaging applications", Dec. (2004), Proceedings of SPIE, vol. 5329.

Kevin Belfield, et al., "Reactive two-photon fluorescent probes for biological imaging", Dec. (2004), pp. 91-95, Proceedings of SPIE, vol. 5329.

* cited by examiner

*Primary Examiner*—Joseph K. McKane
*Assistant Examiner*—Michael P Barker
(74) *Attorney, Agent, or Firm*—Brian S. Steinberger; Joyce P. Morlin; Law Offices of Brian S, Steinberger, P.A.

(57) ABSTRACT

Fluorescent dyes and probes are key components in multiphoton based fluorescence microscopy imaging of biological samples. In order to address the demand for better performing dyes for two-photon based imaging, a new series of reactive fluorophores tailored for multiphoton imaging has been disclosed. These fluorophores are based upon the fluorene ring system, known to exhibit high fluorescence quantum yields, typically >0.7, and possess high photostability. They have been functionalized with moieties to act, e.g., as efficient amine-reactive fluorescent probes for the covalent attachment onto, e.g., proteins and antibodies. The synthesis and the single-photon spectral characteristics, as well as measured two-photon absorption cross sections of the reactive fluorophores in solution are presented. Spectral characterizations of bovine serum albumin (BSA) conjugated with the new reactive probe is presented.

9 Claims, 6 Drawing Sheets

REACTIVE PROBES FOR TWO-PHOTON FLUORESCENT IMAGING AND SENSING

This invention claims priority based on U.S. Provisional Application Ser. No. 60/571,202 filed on May 14, 2004 and the invention was funded in part by the National Science Foundation (ECS-9970078, ECS-0217932, DMR-9975773), the National Research Council (COBASE), the Research Corporation, and the donors of The Petroleum Research Fund of the American Chemical Society and the Florida Hospital Gala Endowed Program for Oncologic Research Award.

FIELD OF INVENTION

This invention relates to two-photon fluorescence imaging, and in particular to a class of fluorescence probes having the properties of high fluorescence quantum yields, high photon absorptivity and high photostability.

BACKGROUND AND PRIOR ART

Two-photon laser scanning fluorescence microscopy, first demonstrated by Denk et al. in 1990, is based on the simultaneous absorption of two low-energy photons by a fluorophore in a single quantum event to induce an electronic excitation that is normally accomplished by a single high-energy photon. The main advantage of two-photon microscopy over conventional linear microscopy stems from the high spatial localization of this excitation event due to the quadratic relation between the excitation and illumination intensity. Practically, this means fluorescence occurs only at the beam focus and as ultrafast, pulsed, near-IR laser irradiation is used as the excitation source, deeper imaging into optically thick tissue, with restricted photobleaching and phototoxicity to the exposed area of the specimen is achieved. The tenants of two-photon absorption (2PA) enables investigations of complex biological problems and experiments on living samples not possible with other imaging techniques, and highlighted examples of its use in the medicinal and biological research areas have been noted.

Two-photon fluorescence methods and techniques have advanced to yield sophisticated imaging techniques, but conventional UV-excitable fluorophores not optimized for efficient 2PA continue to be utilized. Two-photon photophysical characterization databases for commonly used fluorophores and bio-indicators have been reported. Many of these compounds exhibit relatively low two-photon absorption cross-sections ($\delta$), on the order of 10 to 100 GM units. The ($\delta$) parameter is an indicator of the two-photon absorption efficiency, and only recently has research been reported on the design and development of very efficient 2PA dyes on the order of >10 GM units. Much of the synthetic efforts have focused on preparing new organic dyes for a range of applications, as molecules specifically engineered for two-photon excitation may significantly outperform standard fluorophores optimized for single photon excitation. However, the identification and availability of optimized 2PA fluorophores specifically tailored for labeling biomolecules for two-photon fluorescence imaging studies are rare. To date, reactive fluorescent dyes exhibiting high 2PA cross-sections, specifically to covalently modify biomolecules have not been reported. Hence, the need to incorporate reactive, efficient 2PA fluorophores for covalent attachment onto biomolecules within the fluorophore design strategy seems timely and fulfills an appropriate need which coincides with increasing usage of two-photon excitation fluorescence imaging applications in the life sciences.

Previous studies have reported on the design and development of fluorene-based organic dyes with very efficient two-photon absorption and fluorescence emission properties and their use in data storage and sensing applications.

It would be highly desirable to provide a two-photon probe with the properties of high fluorescence quantum yields, of high photon absorptivity and high photostability.

SUMMARY OF THE INVENTION

The primary objective of this invention is to provide a two-photon probe with the property of high fluorescence quantum yields.

The secondary objective of this invention is to provide a two-photon probe with the property of high photon absorptivity.

The third objective of this invention is to provide a fluorophore probe with the property of high photostability.

Novel two-photon probes according to this invention are used in a method of multiphon imaging comprising the use of reactive fluorophores having a fluorene ring system wherein said fluorophores are functionalized with moieties having the properties of covalent attachment onto proteins, antibodies, DNA, and RNA.

In the present invention, a preferred reactive fluorophore has the structural formula and a preferred dye adduct has the structural formula:

A BSA model bioconjugate has the structural formula and a hydrophilic amine-reactive fluorophore has the structural formula in the present invention.

A more preferred dye adduct of the present invention is hydrophilic and has the structural formula

A preferred hydrophilic protein bioconjugate of the present invention has the structural formula A preferred method of multiphon imaging includes the use of reactive fluorophores upon a fluorene ring system, more preferably, the flurophores are functionalized with moieties having the properties of covalent attachment onto proteins and antibodies.

It is also preferred that a Ti:sapphire laser be used to provide for the multiphoton imaging.

A preferred generic Two-Photon Reactive Probe Structure has the formula $R^1$, $R^2$, X, and Y are all functionality tailored for specific applications wherein $R^1$ and $R^2$ are selected from the group, such that $R^1$ and $R^2$, at each occurrence, are independently $C_1$-$C_{16}$ alkyl, $C_1$-$C_{10}$ haloalkyl, —$(CH_2)_{1-9}CO_2H$, —$(CH_2)_{1-9}CO_2(C_1$-$C_6$ alkyl), —$(CH_2CH_2O)_{1-10}H$, —$(CH_2CH_2O)_{1-10}(C_1$-$C_6$ alkyl); —$(CH_2CH_2O)_{1-10}(CO_2C_1$-$C_6$ alkyl); —$(CH_2CH_2O)_{1-10}(CO_2H)$; or —$(CH_2CH_2O)_{1-10}(CO_2$-N-succinimidyl);

X is selected from the group:
—N=C=S, —N=C=O, $CO_2H$, —N-succinimidyl, —P(=O)(OH)$_2$, —P(=O)(OH)$_2$, —P(=O)(OH)(O—$C_1$-$C_6$ alkyl), —P(=O)Cl$_2$, P(=O)F$_2$, —P(=O)(F)(O—$C_1$-$C_6$ alkyl), —P(=O)(Cl)(O—$C_1$-$C_6$ alkyl), P(=O)Br$_2$, or —P(=O)(Br)(O—$C_1$-$C_6$ alkyl);

wherein Y is selected from the group:
—$NH_2$, —NH($C_1$-$C_6$ alkyl), —N($C_1$-$C_6$ alkyl)$_2$, —N($C_1$-$C_6$ alkyl)$_2$, —NH(aryl), —N(aryl)$_2$, —NHCO($C_1$-$C_4$ alkyl), 2-thiazolyl substituted with 0-2 $R^3$; 2-oxazolyl substituted with 0-2 $R^3$; 2-benzothiazolyl substituted with 0-4 $R^3$; 2-styrlbenzothiazolyl; 2-benzoxazolyl substituted with 0-4 $R^3$; and 2- or 4-pyridyl substituted with 0-4 $R^3$, and N-carbazolyl substituted with 0-4 $R^3$; and $R^3$ is independently amino, hydroxy, halogen, $C_1$-$C_6$ alkoxy, $C_1$-$C_{10}$ alkyl, $C_1$-$C_6$ haloalkyl, SH, $SCH_3$, —NH($C_1$-$C_6$ alkyl), —N($C_1$-$C_6$ alkyl)$_2$, —NH(aryl), —N(aryl)$_2$, —NHCO($C_1$-$C_4$ alkyl), —N=C=S, —NH(C=S)—O($C_1$-$C_6$ alkyl), —NH(C=S)—NH($C_1$-$C_6$ alkyl), —NH(C=S)—N($C_1$-$C_6$ alkyl)$_2$, —$CO_2H$, or —$CO_2$($C_1$-$C_6$ alkyl).

To more fully understand the scope of the above reaction products, a preferred two-photon fluorphore labeled protein or antibody of the present invention is provided below.

A preferred two-photon fluorphore labeled protein of the present invention has the formula wherein $R^1$ and $R^2$ are selected from the group:
$R^1$ and $R^2$, at each occurrence, are independently $C_1$-$C_{16}$ alkyl, $C_1$-$C_{10}$ haloalkyl, —$(CH_2)_{1-9}CO_2H$, —$(CH_2)_{1-9}CO_2(C_1$-$C_6$ alkyl),
—$(CH_2CH_2O)_{1-10}H$, —$(CH_2CH_2O)_{1-10}(C_1$-$C_6$ alkyl); —$(CH_2CH_2O)_{1-10}(CO_2C_1$-$C_6$ alkyl); —$(CH_2CH_2O)_{1-10}(CO_2H)$; or —$(CH_2CH_2O)_{1-10}(CO_2$—N-succinimidyl;

wherein Y is selected from the group:
—$NH_2$, —NH($C_1$-$C_6$ alkyl), —N($C_1$-$C_6$ alkyl)$_2$, —NH(aryl), —N(aryl)$_2$, —NHCO($C_1$-$C_4$ alkyl), 2-thiazolyl substituted with 0-2 $R^3$; 2-oxazolyl substituted with 0-2 $R^3$; 2-benzothiazolyl substituted with 0-4 $R^3$; 2-styrlbenzothiazolyl; 2-benzoxazolyl substituted with 0-4 $R^3$; and 2- or 4-pyridyl substituted with 0-4 $R^3$, and N-carbazolyl substituted with 0-4 $R^3$; and $R^3$ is independently amino, hydroxy, halogen, $C_1$-$C_6$ alkoxy, $C_1$-$C_{10}$ alkyl, $C_1$-$C_6$ haloalkyl, SH, $SCH_3$, —NH($C_1$-$C_6$ alkyl), —N($C_1$-$C_6$ alkyl)$_2$, —NH(aryl), —N(aryl)$_2$, —NHCO($C_1$-$C_4$ alkyl), —N=C=S, —NH(C=S)—O($C_1$-$C_6$ alkyl), —NH(C=S)—NH($C_1$-$C_6$ alkyl), —NH(C=S)—N($C_1$-$C_6$ alkyl)$_2$, —$CO_2H$, or —$CO_2$($C_1$-$C_6$ alkyl).

The present invention also includes a preferred two-photon fluorphore labeled antibody having the formula wherein $R^1$ and $R^2$ are selected from the group:
$R^1$ and $R^2$, at each occurrence, are independently $C_1$-$C_{16}$ alkyl, $C_1$-$C_{10}$ haloalkyl, —$(CH_2)_{1-9}CO_2H$, —$(CH_2)_{1-9}CO_2(C_1$-$C_6$ alkyl),
—$(CH_2CH_2O)_{1-10}H$, —$(CH_2CH_2O)_{1-10}(C_1$-$C_6$ alkyl); —$(CH_2CH_2O)_{1-10}(CO_2C_1$-$C_6$ alkyl); —$(CH_2CH_2O)_{1-10}(CO_2H)$; or —$(CH_2CH_2O)_{1-10}(CO_2$—N-succinimidyl);

wherein Y is selected from the group:

—NH$_2$, —NH(C$_1$-C$_6$ alkyl), —N(C$_1$-C$_6$ alkyl)$_2$, —NH (aryl), —N(aryl)$_2$, —NHCO(C$_1$-C$_4$ alkyl), 2-thiazolyl substituted with 0-2 R$^3$; 2-oxazolyl substituted with 0-2 R$^3$; 2-benzothiazolyl substituted with 0-4 R$^3$; 2-styrl-benzothiazolyl; 2-benzoxazolyl substituted with 0-4 R$^3$; and 2- or 4-pyridyl substituted with 0-4 R$^3$, and N-carbazolyl substituted with 0-4 R$^3$; and R$^3$ is independently amino, hydroxy, halogen, C$_1$-C$_6$ alkoxy, C$_1$-C$_{10}$ alkyl, C$_1$-C$_6$ haloalkyl, SH, SCH$_3$, —NH(C$_1$-C$_6$ alkyl), —N(C$_1$-C$_6$ alkyl)$_2$, —NH(aryl), —N(aryl)$_2$, —NHCO(C$_1$-C$_4$ alkyl), —N=C=S, —NH(C=S)—O(C$_1$-C$_6$ alkyl), —NH(C=S)—NH(C$_1$-C$_6$ alkyl), —NH(C=S)—N(C$_1$-C$_6$ alkyl)$_2$, —CO$_2$H, or —CO$_2$(C$_1$-C$_6$ alkyl).

Further objects and advantages of this invention will be apparent from the following detailed description of the presently preferred embodiments which are described in the following text.

DETAILED DESCRIPTION OF THE INVENTION

Before explaining the disclosed embodiment of the present invention in detail it is to be understood that the invention is not limited in its application to the details of the particular arrangement shown since the invention is capable of other embodiments. Also, the terminology used herein is for the purpose of description and not of limitation.

To better understand this invention as set forth, recall that the fluorene ring is a δ-conjugated system which allows for facile synthetic manipulation, yielding dyes with tailored spectral properties. Efforts directed towards preparing reactive fluorescent dyes have been initiated with the synthesis of an amine-reactive dye for labeling, e.g., lysine residues on proteins. A model dye-adduct exhibiting high fluorescence quantum yield (QY=0.74) was also prepared by reacting an amine-reactive dye with n-butyl-amine to test its reactivity as an amine-reactive fluorescent label and determine its spectroscopic properties. Additionally, a model protein bioconjugate was prepared with the reactive fluorophore and bovine serum albumin. Finally, a hydrophilic derivative of an amine-reactive dye was prepared to obtain a more water-soluble dye. The foregoing will become apparent upon reading the following experimental discussion.

EXPERIMENTAL

Figure 1:
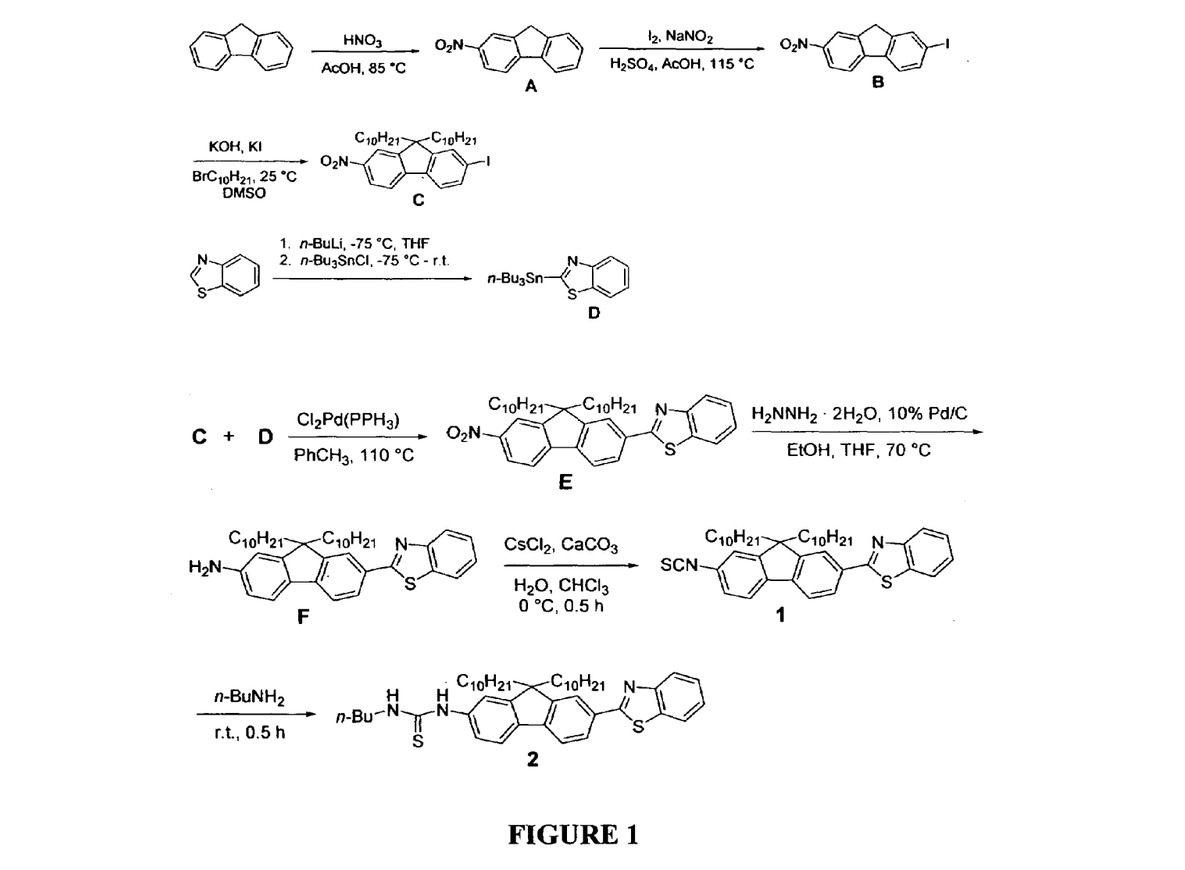
FIG. 1 shows the preparation of a dye adduct and model bioconjugate with a reaction 2PA fluorophore.

Reference should now be made to FIG. 1. The synthesis of an amine reactive fluorescent dye (1) was prepared as a biological labeling probe (Scheme 1). Intermediate compounds A-F have been described previously in the literature. Preparation of reactive probe 1, from aminofluorene F, was performed quantitatively, following the literature protocol. The procedure for preparation of reactive probe 1 is shown in FIG. 1. Compound (1) was prepared as an amine-reactive fluorescent dye, containing the isothiocyanate functionality that can react with primary amine groups present on protein molecules. A model dye-adduct (2) was also prepared by reacting (1) with n-butyl-amine to test its reactivity as an amine-reactive fluorescent label (FIG. 1). Preparation of the model adduct allowed for facile single- and two-photon spectroscopic characterizations that more closely resembles the bioconjugate than that of the reactive fluorophore alone.

Figure 2:
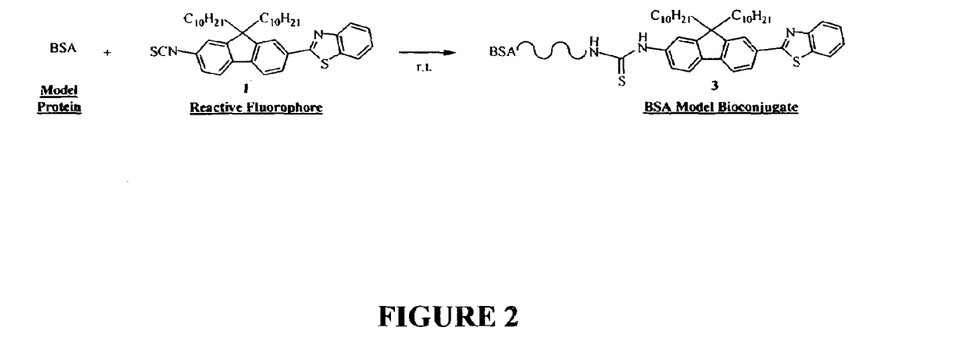
FIG. 2 shows the preparation of a model bioconjugate with reactive fluorophore

The amine-reactive fluorescent dye (1) was used to prepare a bioconjugate (3) with bovine serum albumin (BSA) protein as a model biomolecule (which is shown in FIG. 2). The use of BSA, an inexpensive protein that has been extensively characterized, is ideal for establishing optimal conditions to obtain a model bioconjugate allowing for subsequent spectroscopic characterization.

The amine reactive reagent (isothiocyanate functional group) reacts with non-protonated aliphatic amine groups, including the N-terminus of proteins and the ε-amino groups of lysines (pKa≈10.5). A typical protocol for the conjugation was followed in an amine-free buffer with a slightly basic pH (pH=9.0). The amine reactive dye (1) was dissolved in DMSO, immediately prior to addition into the stirring BSA protein solution. The reaction mixture was allowed to stir at room temperature, after which it was passed through a Sephadex G-25 gel filtration column pre-swollen with water and equilibrated with phosphate buffer saline (PBS, pH 7.2) solution. Small fractions, eluted with the PBS solution were collected into sterile plastic tubes, and the UV-visible absorption and steady-state fluorescence emission spectra of the bioconjugate were obtained.

Two different molar ratios of the reactive dye to protein were performed to assess the reactivity of the dye for its degree of labeling (DOL) (Table 1). The degree of labeling was estimated using average values from standard equations obtained from reference 25.

TABLE 1

Variable degree of labeling obtained by changing the molar ratios of the reactive dye to BSA.

| BSA | Reactive fluorophore | Dye:Protein mol ratio | Reaction time | DOL (mol dye:mol protein) |
|---|---|---|---|---|
| 1.53E-8 mol | 1.53E-7 mol | 10:1 | 1 h | 3.4 |
| 1.53E-8 mol | 7.7E-8 mol | 5:1 | 1 h | 2.4 |
| 1.53E-8 mol | 7.7E-8 mol | 5:1 | 2 h | 2.2 |

RESULTS AND DISCUSSION OF THE INVENTION

Figure 4:
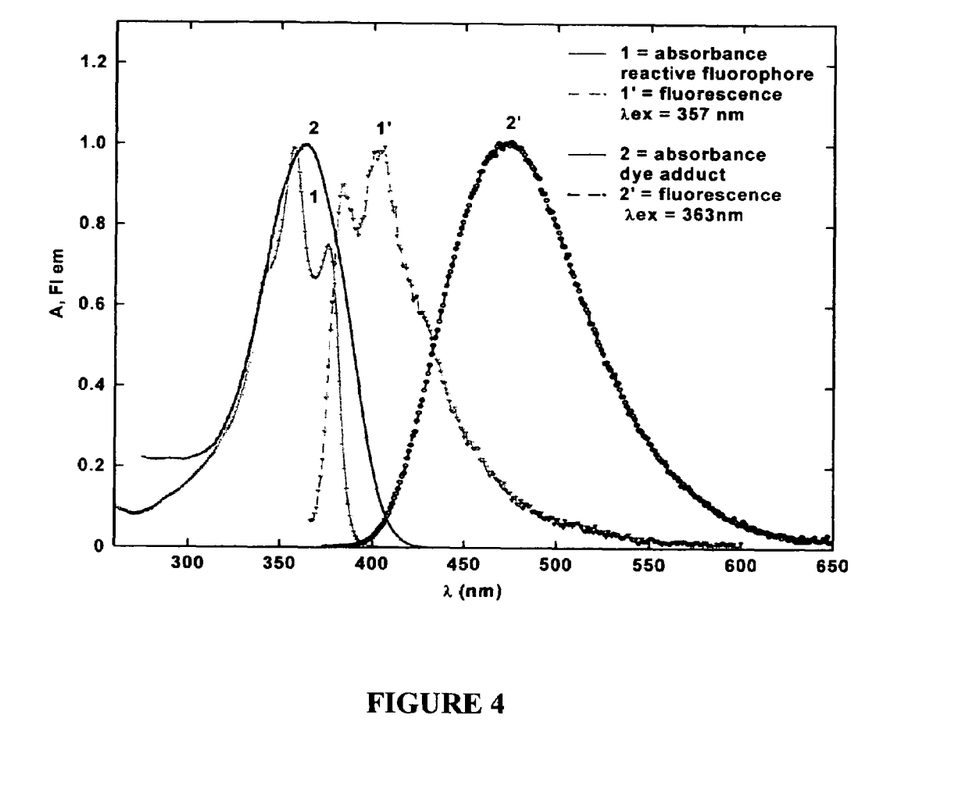
FIG. 4 shows normalized UV-visible absorbance (1, 2) and fluorescence emission (1', 2'; excitation line indicated) spectra of the reactive fluorophore 1 and the dye adduct 2.

The normalized UV-visible absorption and steady-state fluorescence emission spectra of the free reactive fluorophore (1) and the dye adduct (2) in DMSO are shown in FIG. 4. The free reactive fluorophore exhibits two absorption maxima at approximately 357 and approximately 375 nm, along with two emission maxima at approximately 384 and approximately 404 nm. The dye adduct instead exhibits a single absorption maximum at approximately 363 nm with an emission maximum at approximately 403 nm, and is well resolved from that of its absorption spectrum, with minimal spectral overlap. The fluorescence quantum yield (Rhadamine 6G in ethanol as a standard) of the reactive fluorophore in DMSO was approximately 0.02, while that of the dye adduct in DMSO increased significantly to approximately 0.74, indicating the fluorescence of the reactive dye should be restored upon conjugation to a biomolecule.

Figure 5A:
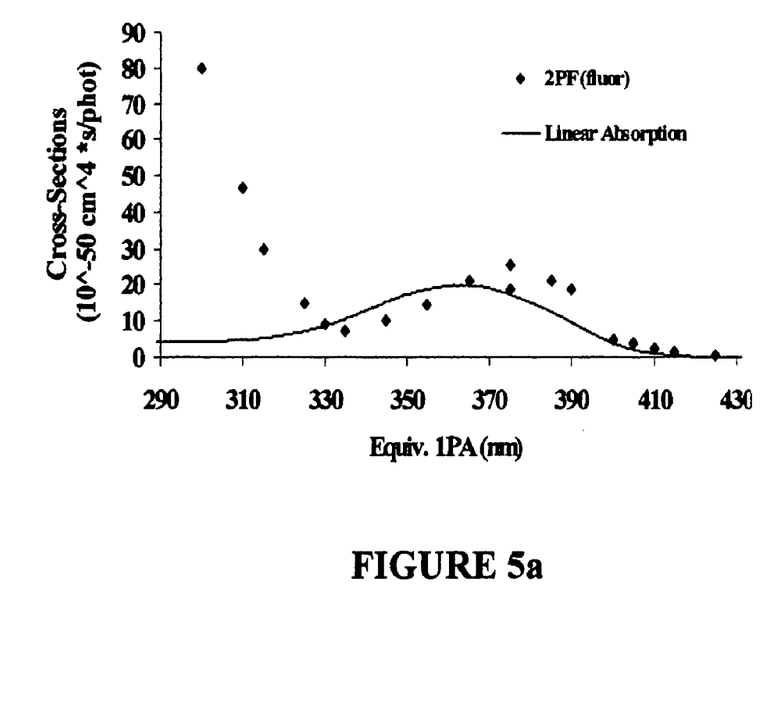
FIG. 5a shows the two-photon absorption for the dye adduct.

The two-photon absorption cross sections (from two-photon fluorescence measurements) for the dye adduct in DMSO was obtained under femtosecond (fs) near IR irradiation (FIG. 5a). The linear, single photon absorption spectrum is shown as the line profile, while the two-photon absorption cross sections were measured at wavelengths that were twice that of the linear absorption, and are shown as the data points. The y-axis is shown as two near-IR photons used to obtain the cross section converted to an equivalent single photon wavelength. The two-photon absorption cross section at the energy of the linear absorption maximum near 370 nm is approximately 25 GM units. Interestingly, while the linear absorption spectrum for the compound does not display any significant absorption at the shorter wavelengths, the value of the two-photon absorption cross section increases. To ensure the dye adduct undergoes 2PA, a log-log plot of the fs pump power to that of the integrated fluorescence was constructed. As can be seen from FIG. 5b, the slopes from the measurements confirm the quadratic dependence characteristic of fluorescence obtained from two-photon absorption.

Figure 5B:
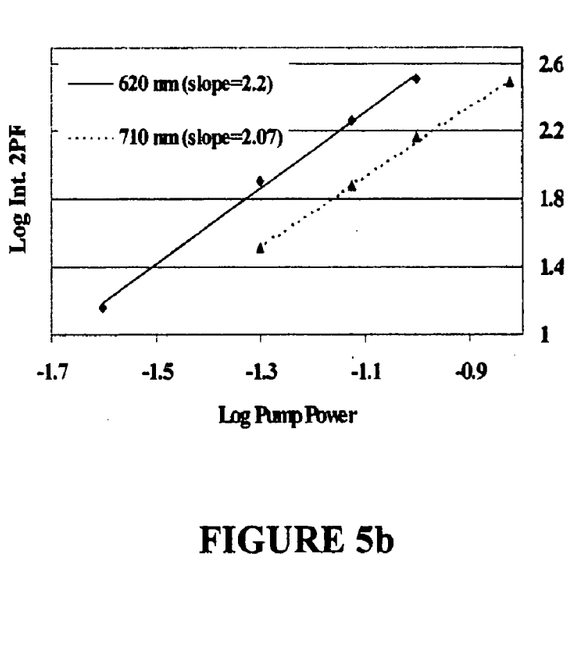
FIG. 5b shows a log-log plot of the dye adduct integrated fluorescence.

FIGS. 5a-5b show the two-photon cross section of the dye adduct in FIG. 5a, and the log-log plot of its integrated fluorescence as a function of pump power variation at two different fs excitation wavelengths in FIG. 5b.

Figure 6:
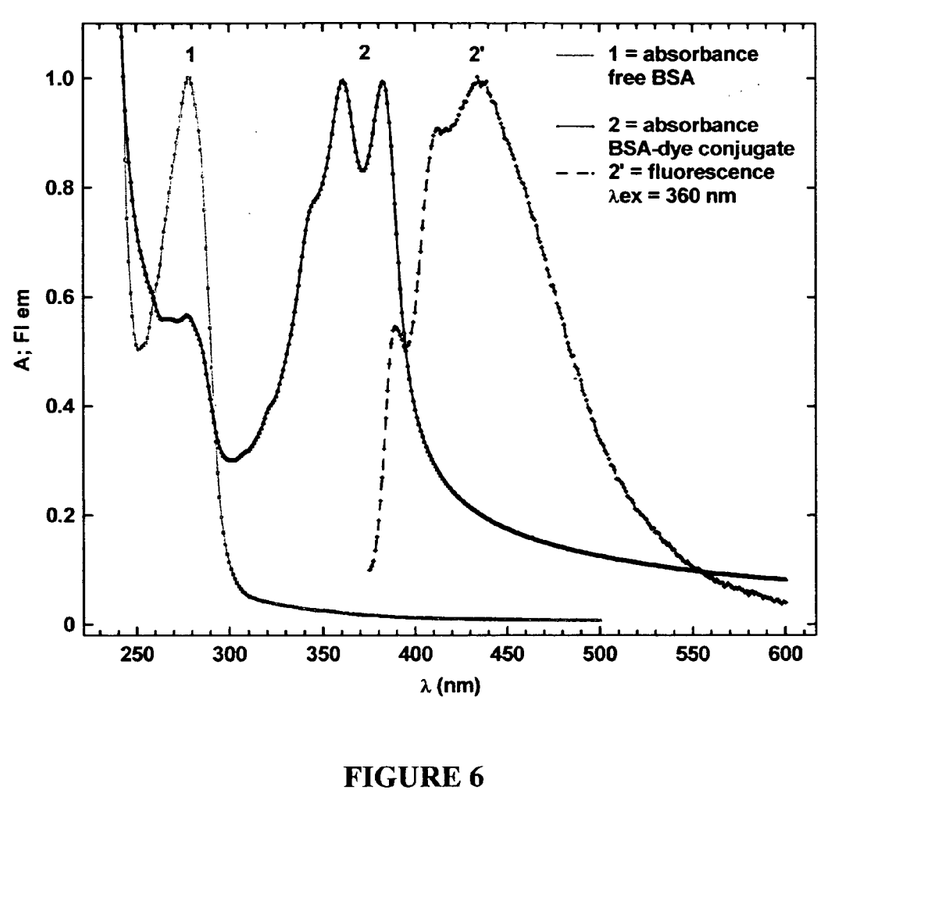
FIG. 6 shows normalized absorption spectra of the free BSA protein and BSA-dye conjugate (1 and 2) and steady-state fluorescence emission spectrum of the BSA-dye conjugate (2').

The normalized absorption and steady-state fluorescence emission spectra of the BSA-dye bioconjugate (3) in PBS buffer (pH 7.2) is shown in FIG. 6. For reference, the absorption spectrum of the free BSA protein in PBS solution is also shown. The BSA-dye conjugate displays absorption peaks corresponding to that of the BSA protein in the shorter wavelength range ($\delta_{max}$=280 nm), as well as that of the fluorescent dye in the longer absorption range ($67_{maxuma}$=360 nm and 380 nm). The fluorescence emission of the bioconjugate is broad and exhibits an appreciable Stoke's shift. An appreciable bathochromic shift in the fluorescence emission was observed in the BSA-dye conjugate relative to that of the free reactive fluorophore, and with a similar broadening observed in the absorption profile, the fluorescence emission was also broader than that of the free fluorophore. The observed Stoke's shift in the free dye was about 45 nm, while that of the BSA-dye conjugate was much greater (Stoke's shift=73 nm upon $\delta_{ex}$=360 nm, and 53 nm upon $\delta_{ex}$=380 nm). The fluorescence emission profile of the BSA-dye conjugate upon excitation at $\delta_{ex}$=360 nm and $\delta_{ex}$=380 nm yielded similar fluorescence intensities.

Figure 3:
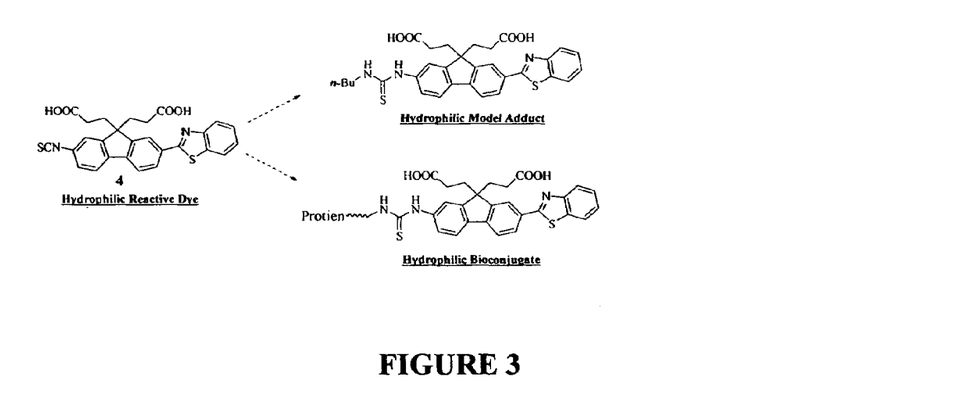
FIG. 3 shows the structure of a hydrophilic amine-reaction fluorophore (4) for the preparation of a model adduct and bioconjugate.

The spectroscopic profiles of the BSA-dye conjugate validate the use of the reactive dye (1) to form bioconjugates with protein biomolecules for fluorescence imaging applications. However, attempts to conjugate the dye onto an anti-BSA antibody (Molecular Probes) were unsuccessful. The two hydrophobic alkyl chains on the fluorene ring may have interfered with efficient conjugation onto the higher molecular weight of the antibody (~150 kDa) relative to that of the smaller protein (~65 kDa). Hence, a more hydrophilic derivative of an amine-reactive dye was prepared (compound 4 of FIG. 3). Substitution of the alkyl groups on the fluorene ring with carboxylates should enhance the water solubility of the reactive de, and is expected to improve its conjugation to a wider range of biomolecules in aqueous media. The FT-IR spectrum of the hydrophilic reactive dye (4) displayed a strong NCS stretch at 2118 cm-1, indicating the presence of the amine-reactive functionality. Efforts to prepare appropriate adducts and bioconjugates with the hydrophilic dye (4) are currently underway.

A new series of reactive fluorophores have been prepared to covalently label biomolocules for multiphoton imaging. These fluorophores are based upon the fluorene ring system and exhibit high fluorescence quantum yields upon bioconjugation (~0.7). They have been functionalized with moieties to act, e.g., as efficient amine-reactive fluorescent probes for the covalent attachment onto, e.g., proteins and antibodies. A bovine serum albumin (BSA) conjugate with a new reactive probe has been demonstrated. Additionally, a hydrophilic reactive fluorophore has been prepared, expected to be more efficient for labeling biomaterials in aqueous media. These efficient two-photon absorbing reactive dyes are expected to be versatile probes for multiphoton bio-imaging applications.

In summary, there is disclosed numerous structures and the preparation provided by the teachings of this invention: the dye adduct 1
Reactive Fluorophore 2
Dye Adduct (Model Compound)

The dye adducts that are hydrophilic and have the structural formulae

Hydrophilic Model Adduct

4
Hydrophilic Reactive Dye

Hydrophilic Bioconjugate a BSA model bioconjugate having the structural formula

1
Reactive Fluorophore

3
BSA Model Bioconjugate

A hydrophilic amine-reactive fluorophore having the structural formula

4
Hydrophilic Reactive Dye

Generic Two-Photon Reactive Probe Structure $R^1$, $R^2$, X, and Y are all functionality tailored for specific applications wherein $R^1$ and $R^2$ are selected from the group:
  $R^1$ and $R^2$, at each occurrence, are independently $C_1$-$C_{16}$ alkyl, $C_1$-$C_{10}$ haloalkyl, —$(CH_2)_{1-9}CO_2H$, —$(CH_2)_{1-9}CO_2(C_1$-$C_6$ alkyl), —$(CH_2CH_2O)_{1-10}H$, —$(CH_2CH_2O)_{1-10}(C_1$-$C_6$ alkyl); —$(CH_2CH_2O)_{1-10}(CO_2C_1$-$C_6$ alkyl); —$CH_2CH_2O)_{1-10}(CO_2H)$; or —$(CH_2CH_2O)_{1-10}(CO_2$—N-succinimidyl);

wherein X is selected from the group:
  —N=C=S, —N=C=O, $CO_2H$, —N-succinimidyl, —P(=O)(OH)$_2$, —P(=O)(OH)(O—$C_1$-$C_6$ alkyl), —P(=O)Cl$_2$, P(=O)F$_2$, —P(=O)(F)(O—$C_1$-$C_6$ alkyl), —P(=O)(Cl)(O—$C_1$-$C_6$ alkyl), P(=O)Br$_2$, or —P(=O)(Br)(O—$C_1$-$C_6$ alkyl);

wherein Y is selected from the group:
  —NH$_2$, —NH($C_1$-$C_6$ alkyl), —N($C_1$-$C_6$ alkyl), —N($C_1$-$C_6$ alkyl)$_2$, —NH(aryl), —N(aryl)$_2$, —NHCO($C_1$-$C_4$ alkyl), 2-thiazolyl substituted with 0-2 $R^3$; 2-oxazolyl substituted with 0-2 $R^3$; 2-benzothiazolyl substituted with 0-4 $R^3$; 2-styrlbenzothiazolyl; 2-benzoxazolyl substituted with 0-4 $R^3$; and 2- or 4-pyridyl substituted with 0-4 $R^3$, and N-carbazolyl substituted with 0-4 $R^3$; and $R^3$ is independently amino, hydroxy, halogen, $C_1$-$C_6$ alkoxy, $C_1$-$C_{10}$ alkyl, $C_1$-$C_6$ haloalkyl, SH, $SCH_3$, —NH($C_1$-$C_6$ alkyl), —N($C_1$-$C_6$ alkyl)$_2$, —NH(aryl), —N(aryl)$_2$, —NHCO($C_1$-$C_4$ alkyl), —N=C=S, —NH(C=S)—O($C_1$-$C_6$ alkyl), —NH(C=S)—NH($C_1$-$C_6$ alkyl), —NH(C=S)—N($C_1$-$C_6$ alkyl)$_2$, —$CO_2H$, or —$CO_2$($C_1$-$C_6$ alkyl).

Figure 7:
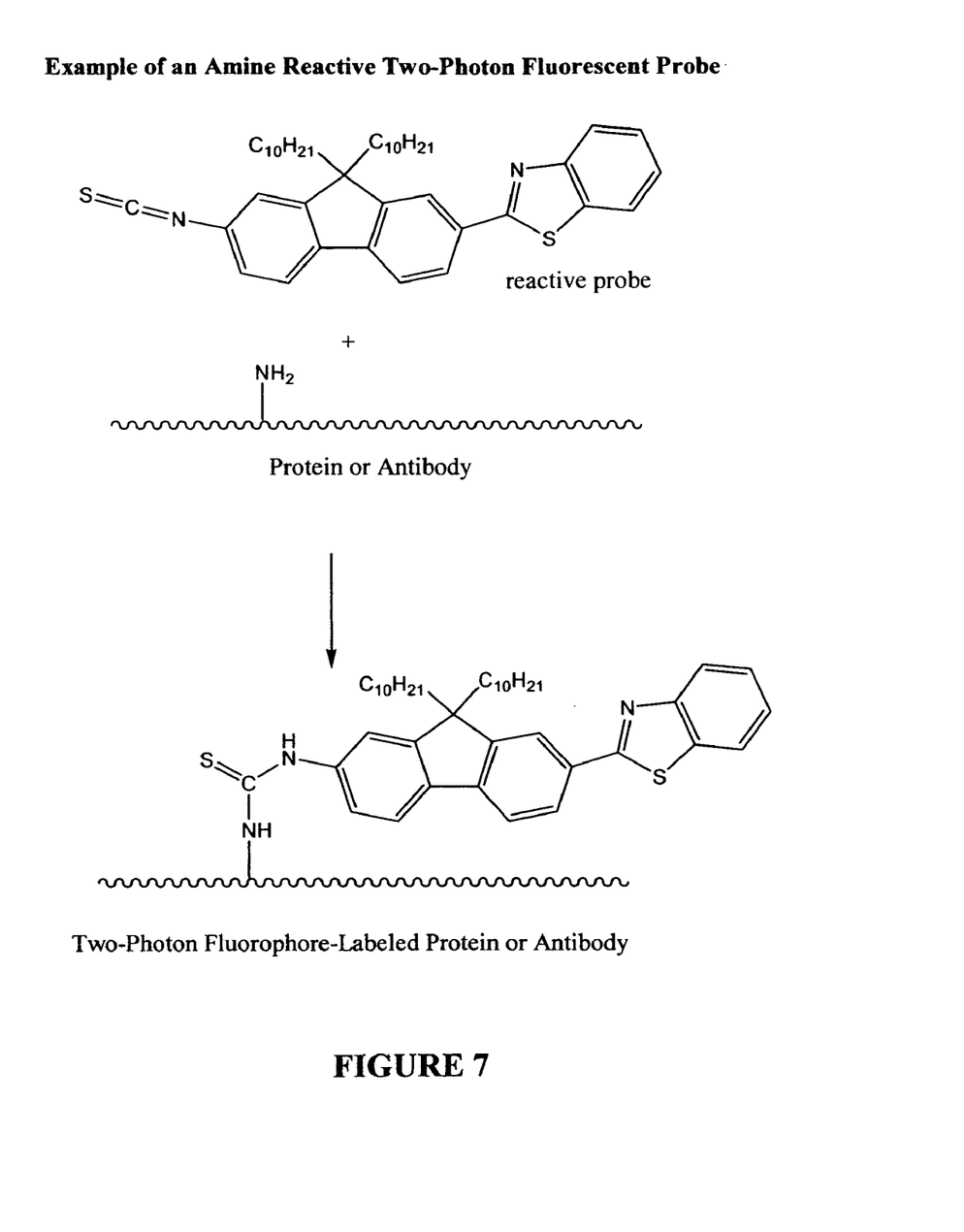
FIG. 7 is an example of an amine reaction two-photon fluorescent probe of the present invention.

FIG. 7 and the example below are further illustrative of the scope of this invention as an amine reactive two-photon fluorescent probe.

Example of an Amine Reactive Two-Photon Fluorescent Probe

Two-Photon Fluorophore-Labeled Protein or Antibody

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A reactive fluorophore of the structural formula

2. A dye adduct of the structural formula

3. A BSA model bioconjugate of the structural formula

4. A hydrophilic amine-reactive fluorophore of the structural formula

5. An Adduct according to claim 2 which is hydrophilic and of the structural formula 6. A hydrophilic protein bioconjugate of the structural formula 7. A Generic Two-Photon Reactive Probe Structure of the formula wherein $R^1$, $R^2$, X, and Y are all functionality tailored for specific applications; and

$R^1$ and $R^2$, at each occurrence, are independently $C_1$-$C_{16}$ alkyl, $C_1$-$C_{10}$ haloalkyl, —$(CH_2)_{1-9}CO_2H$, —$(CH_2)_{1-9}CO_2(C_1$-$C_6$ alkyl), —$(CH_2CH_2O)_{1-10}H$, —$(CH_2CH_2O)_{1-10}(C_1$-$C_6$ alkyl); —$(CH_2CH_2O)_{1-10}(CO_2C_1$-$C_6$ alkyl); —$(CH_2CH_2O)_{1-10}(CO_2H)$; or —$(CH_2CH_2O)_{1-10}(CO_2$—N-succinimidyl; and X is selected from the group:
—N=C=S, —N=C=O, CO$_2$H, —N-succinimidyl, —P(=O)(OH)$_2$, —P(=O)(OH)(O—C$_1$-C$_6$ alkyl), —P(=O)Cl$_2$, P(=O)F$_2$, —P(=O)(F)(O—C$_1$-C$_6$ alkyl), —P(=O)(Cl)(O—C$_1$-C$_6$ alkyl), P(=O)Br$_2$, or —P(=O)(Br)(O—C$_1$-C$_6$ alkyl); and Y is selected from the group:
—NH$_2$, —NH(C$_1$-C$_6$ alkyl), —N(C$_1$-C$_6$ alkyl)$_2$, —NH(aryl), —N(aryl)$_2$, —NHCO(C$_1$-C$_4$ alkyl), 2-thiazolyl substituted with 0-2 R$^3$; 2-oxazolyl substituted with 0-2 R$^3$; 2-benzothiazolyl substituted with 0-4 R$^3$; 2-styrlbenzothiazolyl; 2-benzoxazolyl substituted with 0-4 R$^3$; and 2- or 4-pyridyl substituted with 0-4 R$^3$, and N-carbazolyl substituted with 0-4 R$^3$; and R$^3$ is independently amino, hydroxy, halogen, C$_1$-C$_6$ alkoxy, C$_1$-C$_{10}$ alkyl, C$_1$-C$_6$ haloalkyl, SH, SCH$_3$, —NH(C$_1$-C$_6$ alkyl), —N(C$_1$-C$_6$ alkyl)$_2$, —NH(aryl), —N(aryl)$_2$, —NHCO(C$_1$-C$_4$ alkyl), —N=C=S, —NH(C=S)—O(C$_1$-C$_6$ alkyl), —NH(C=S)—NH(C$_1$-C$_6$ alkyl), —NH(C=S)—N(C$_1$-C$_6$ alkyl)$_2$, —CO$_2$H, or —CO$_2$(C$_1$-C$_6$ alkyl).

8. A two-photon fluorphore labeled protein of the formula wherein R$^1$ and R$^2$ are selected from the group wherein:
R$^1$ and R$^2$, at each occurrence, are independently C$_1$-C$_{16}$ alkyl, C$_1$-C$_{10}$ haloalkyl, —(CH$_2$)$_{1-9}$CO$_2$H, —(CH$_2$)$_{1-9}$CO$_2$(C$_1$-C$_6$ alkyl), —(CH$_2$CH$_2$O)$_{1-10}$H, —(CH$_2$CH$_2$O)$_{1-10}$(C$_1$-C$_6$ alkyl); —(CH$_2$CH$_2$O)$_{1-10}$(CO$_2$C$_1$-C$_6$ alkyl); —(CH$_2$CH$_2$O)$_{1-10}$(CO$_2$H); or —(CH$_2$CH$_2$O)$_{1-10}$(CO$_2$—N-succinimidyl; and Y is selected from the group:
—NH$_2$, —NH(C$_1$-C$_6$ alkyl), —N(C$_1$-C$_6$ alkyl)$_2$, —NH(aryl), —N(aryl)$_2$, —NHCO(C$_1$-C$_4$ alkyl), 2-thiazolyl substituted with 0-2 R$^3$; 2-oxazolyl substituted with 0-2 R$^3$; 2-benzothiazolyl substituted with 0-4 R$^3$; 2-styrlbenzothiazolyl; 2-benzoxazolyl substituted with 0-4 R$^3$; and 2- or 4-pyridyl substituted with 0-4 R$^3$, and N-carbazolyl substituted with 0-4 R$^3$; and R$^3$ is independently amino, hydroxy, halogen, C$_1$-C$_6$ alkoxy, C$_1$-C$_{10}$ alkyl, C$_1$-C$_6$ haloalkyl, SH, SCH$_3$, —NH(C$_1$-C$_6$ alkyl), —N(C$_1$-C$_6$ alkyl)$_2$, —NH(aryl), —N(aryl)$_2$, —NHCO(C$_1$-C$_4$ alkyl), —N=C=S, —NH(C=S)—O(C$_1$-C$_6$ alkyl), —NH(C=S)—NH(C$_1$-C$_6$ alkyl), —NH(C=S)—N(C$_1$-C$_6$ alkyl)$_2$, —CO$_2$H, or —CO$_2$(C$_1$-C$_6$ alkyl).

9. A two-photon fluorphore labeled antibody of the formula wherein R$^1$ and R$^2$ are selected from the group wherein:
R$^1$ and R$^2$, at each occurrence, are independently C$_1$-C$_{16}$ alkyl, C$_1$-C$_{10}$ haloalkyl, —(CH$_2$)$_{1-9}$CO$_2$H, —(CH$_2$)$_{1-9}$CO$_2$(C$_1$-C$_6$ alkyl), —(CH$_2$CH$_2$O)$_{1-10}$H, —(CH$_2$CH$_2$O)$_{1-10}$(C$_1$-C$_6$ alkyl); —(CH$_2$CH$_2$O)$_{1-10}$(CO$_2$C$_1$-C$_6$ alkyl); —(CH$_2$CH$_2$O)$_{1-10}$(CO$_2$H); or —(CH$_2$CH$_2$O)$_{1-10}$(CO$_2$—N-succinimidyl; and Y is selected from the group:
—NH$_2$, —NH(C$_1$-C$_6$ alkyl), —N(C$_1$-C$_6$ alkyl)$_2$, —NH(aryl), —N(aryl)$_2$, —NHCO(C$_1$-C$_4$ alkyl), 2-thiazolyl substituted with 0-2 R$^3$; 2-oxazolyl substituted with 0-2 R$^3$; 2-benzothiazolyl substituted with 0-4 R$^3$; 2-styrlbenzothiazolyl; 2-benzoxazolyl substituted with 0-4 R$^3$; and 2- or 4-pyridyl substituted with 0-4 R$^3$, and N-carbazolyl substituted with 0-4 R$^3$; and R$^3$ is independently amino, hydroxy, halogen, C$_1$-C$_6$ alkoxy, C$_1$-C$_{10}$ alkyl, C$_1$-C$_6$ haloalkyl, SH, SCH$_3$, —NH(C$_1$-C$_6$ alkyl), —N(C$_1$-C$_6$ alkyl)$_2$, —NH(aryl), —N(aryl)$_2$, —NHCO(C$_1$-C$_4$ alkyl), —N=C=S, —NH(C=S)—O(C$_1$-C$_6$ alkyl), —NH(C=S)—NH(C$_1$-C$_6$ alkyl), —NH(C=S)—N(C$_1$-C$_6$ alkyl)$_2$, —CO$_2$H, or —CO$_2$(C$_1$-C$_6$ alkyl).

* * * * *